United States Patent [19]

Olsson et al.

[11] Patent Number: 4,840,167
[45] Date of Patent: Jun. 20, 1989

[54] RESPIRATOR AND A METHOD OF UTILIZING THE RESPIRATOR TO PROMOTE BLOOD CIRCULATION

[75] Inventors: Sven G. Olsson, Soedra Sandby; Björn Jonson, Lund, both of Sweden

[73] Assignee: Siemens Elema AB, Sweden

[21] Appl. No.: 38,494

[22] Filed: Apr. 15, 1987

Related U.S. Application Data

[60] Division of Ser. No. 908,949, Sep. 16, 1986, Pat. No. 4,676,232, Continuation of Ser. No. 552,776, Nov. 17, 1983, abandoned.

[30] Foreign Application Priority Data

Nov. 19, 1982 [DE] Fed. Rep. of Germany ....... 3242814

[51] Int. Cl.⁴ ............................................. A61H 31/00
[52] U.S. Cl. .................................. 128/28; 128/30.2
[58] Field of Search ................. 128/28, 30, 30.2, 38

[56] References Cited

U.S. PATENT DOCUMENTS

| | | |
|---|---|---|
| 2,588,192 | 3/1952 | Akerman et al. |
| 3,461,860 | 8/1969 | Barkalow . |
| 3,461,861 | 8/1969 | Barkalow et al. |
| 3,651,801 | 3/1972 | Kullok . |
| 4,155,356 | 5/1979 | Venegas ............... 128/38 |
| 4,326,507 | 4/1982 | Barkalow . |
| 4,349,015 | 9/1982 | Alferness . |
| 4,397,306 | 8/1983 | Weisfeld et al. ........... 128/28 |
| 4,424,806 | 1/1984 | Newman et al. ........... 128/28 |

FOREIGN PATENT DOCUMENTS

| | | |
|---|---|---|
| 0029352 | 5/1981 | European Pat. Off. . |
| 0057924 | 8/1982 | European Pat. Off. . |
| 1535612 | 7/1968 | France . |

OTHER PUBLICATIONS

Published PCT Application—WO82/03014—published Sep. 16, 1982.

Primary Examiner—Richard J. Apley
Assistant Examiner—J. Welsh
Attorney, Agent, or Firm—Hill, Van Santen, Steadman & Simpson

[57] ABSTRACT

A method and device to support blood circulation during ventilation of the lungs which include controlling the application of the respiratory gases to occur at a particular point in time in the heart activity, and applying a uniform pressure to resist expansion of the thorax cavity to increase pressure on the heart during the heart's systole. The device which applies a respiratory gas and the uniform pressure includes a control device which senses the heart's activity to determine the desired point in time of the heart cycle.

14 Claims, 1 Drawing Sheet

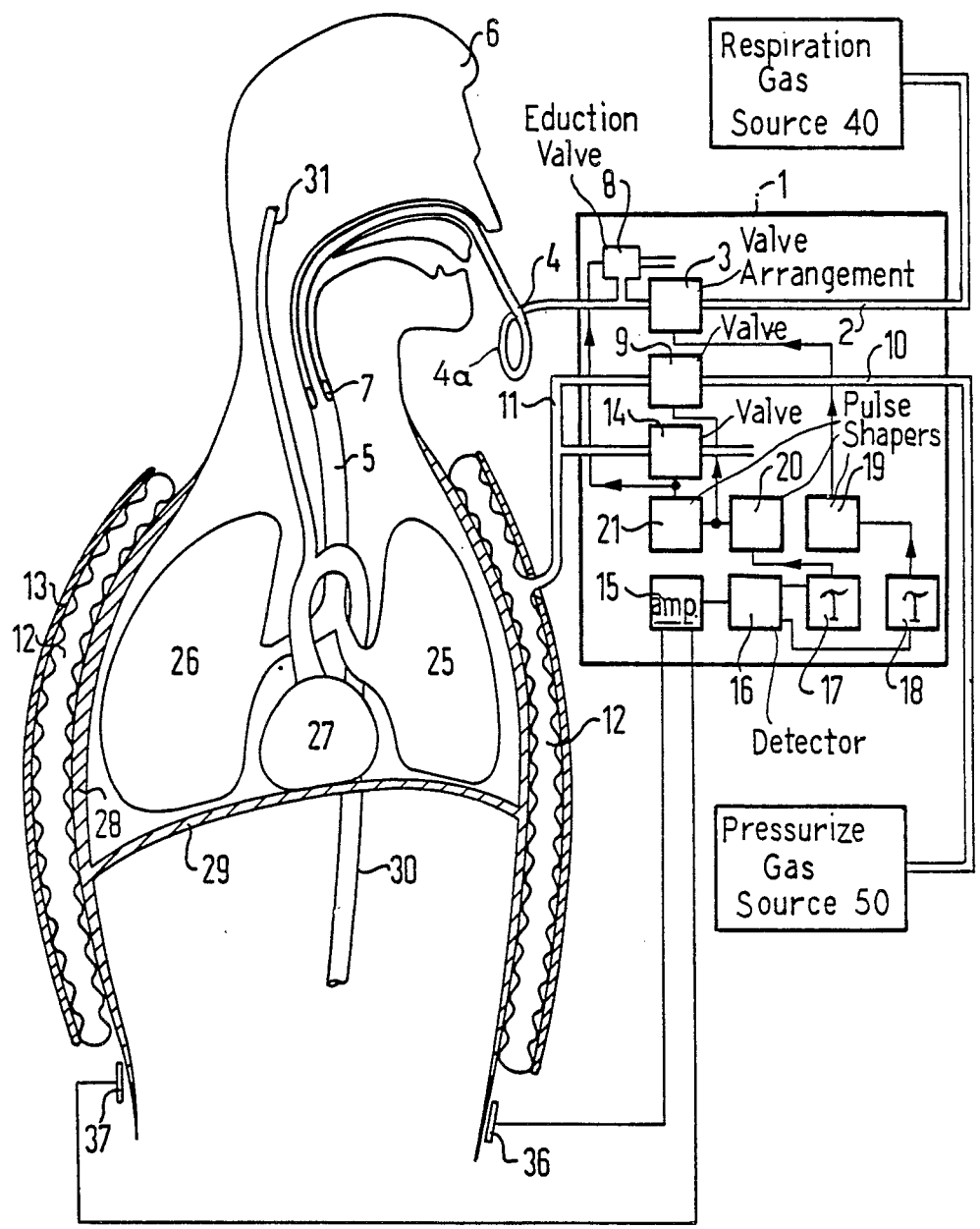

RESPIRATOR AND A METHOD OF UTILIZING THE RESPIRATOR TO PROMOTE BLOOD CIRCULATION

This is a division, of application Ser. No. 908,949, filed 9/16/86 now U.S. Pat. No. 4,676,232, which is a continuation of Ser. No. 552,776 filed 11/17/83 abandoned.

BACKGROUND OF THE INVENTION

The present invention is directed to a method and device for providing respiration to a patient which respiration is synchronized with the heart rhythm and which device and method promote the blood circulation.

In conventional respirator treatments, breathing gas is supplied to the lungs under pressure. This pressure is also partly propagated outside of the lungs into the body cavities in the thorax. It is known that this pressure essentially has a negative influence on the blood circulation. This negative influence is mainly based on the fact that the supply of blood to the heart and the filling of the chambers of the heart during the relaxation phase or expansion of the heart which is known as the diastole is impeded. An inadequate filling of the heart chambers, however, means that the heart cannot generate an adequate beat volume during the following contraction phase which is known as systole. When the heart activity or the blood circulation are already inadequate due to a disease, the negative influences caused by the respiration treatment can have serious consequences.

A series of proposals have already been made in order to reduce these harmful effects on the circulation. It is thus known that an adequate respiration can be achieved with a very high breathing rate, for example, several breaths per second. The volume of each breath is thus decreased and thus the pressure increases which disturb the blood circulation are reduced. This procedure is disclosed in an article in *Proc. Am. Soc. Exp. Biol.* Vol. 38, 1979, p. 951 and a prospectus *Aga Bronchovent*, 318.002 Sv, Nov. 1978: Klain Jet Ventilator.

An additional known improvement can be achieved when the ventilation occurs synchronously with the heart activity so that one breath occurs at every heartbeat or at every second heartbeat. When the inhalation phase is thereby chronologically placed such that it coincides with the systole, an advantageous pressure increase around the heart can be achieved. At the same time, the pressure influence on the heart during the diastole is entirely or at least partially avoided so that the heart's activity is improved overall.

It is also known that the heart chambers can be emptied by means of external compression of the thorax and the heart chambers will again fill up upon removal of this compression. As a result thereof, a certain blood circulation can also be maintained even when the heart does not independently contract or when it is greatly diminished in this function of contraction.

A described possibility for reducing harmful effects on the blood circulation and for promoting the circulation are, however, limited. Given the high frequency ventilation in the heart rhythm, a low breath volume already produces a sufficient respiratioin so that only a slight intrathoracic pressure increase results. Even when this pressure increase is synchronized with the heart rhythm so that it appears during systole, only a slight positive effect is achieved.

Given an increase in the volume of each breath in order to achieve a more effective pressure increase, there exists a risk that the lungs may be damaged by the higher gas pressure to which they have been exposed. In addition, the lungs cannot be emptied fast enough given such a high volume for each breath.

An external compression of the thorax has the disadvantage that this can cause injury to the thorax itself or to internal organs. In addition, the external compression of the thorax may be painful to the patient.

SUMMARY OF THE INVENTION

The present invention is directed to providing a specific method for respiration and ventilation of a patient which respiration is synchronized with the heart rhythm so that the pressure exerted on the heart can be adjustably increased to such a degree that the contraction of the heart can be significantly increased without injury occurring to the lungs and/or to the thorax walls. Another object of the invention consists of providing a respirator with which the desired method can be implemented in a simple and reliable manner.

The objects are inventively achieved in a method comprising the steps of applying a respiratory gas to the lungs of the patient, applying a uniform pressure opposing the expansion of the chest and the abdomen, and synchronizing the step of applying the respiratory gas and applying the uniform force to a particular point of time in the heartbeat cycle so that the pressure rise of the respiratory gas around the heart coincides with the contraction phase of the heart. In addition, the step of synchronizing includes sensing the electrical signals of the heart and utilizing the sensed signals to synchronize the step of applying the respiratory gas and the uniform pressure.

The invention thus proceeds on the basis of the perception that the desired pressure increase around the heart by means of synchronizing the ventilation with the heart rhythm is at least partially cancelled thereby that the chest and the abdomen are allowed to expand during the step of respiration. The invention therefore provides that the expansion is restricted in that a uniform force is exerted on the chest and/or on the abdomen. Upon respiration, thus, the lungs can be partially expanded toward the inside so that the pressure increase around the heart is achieved to the desired degree. The respiration of the patient should thereby occur at a particular point of time in the heart rhythm. That means that one breath should be present per heart cycle or on the other hand, that the breath respectively appears only on every second heartbeat or even more infrequently but synchronous with the heart activity in each case.

It is provided in a further development of the invention in order to optimize the respiration and/or the support of the blood circulation that the point of time and/or the duration of the application of the breathing gas feed and/or pressure are adjustable. Further, the point in time, the duration and the magnitude of the uniform force exerted on the thorax and/or the abdomen is also adjustable.

To accomplish the method, the invention also is directed to a respirator having a first valve control arrangement for controlling the flow of the respiratory gas from a source to and from the patient, means for generating and exerting a uniform pressure on the chest and/or the abdomen, means for sensing the parameters of the heart activity and control means which actuate at least the valves of the first arrangement as a function of the sensed signal.

An advantageously simple embodiment of the respirator provides that the means for applying uniform pressure consist of a rigid hollow body which surrounds at least a part of the chest and/or the abdomen of the patient. This hollow body surrounds the thorax similar to rigid armor. The inside dimension of the hollow body is selected so that a certain amount of expansion of the chest and/or the abdomen is possible before the hollow body is tightly engaged by the patient and prevents further expansion. In order to increase the adaptability in particular to likewise enable possibilities of applying one and the same hollow body for different patients, it is provided in a further development of the invention that the hollow body contains a series of closed chambers consisting of flexible material which are positioned between the thorax and the abdomen of the patient and the hollow body and are filled with a fluid or gas. The inside dimensions, i.e., the size of the hollow body, can thus be practically defined depending on the amount of filling of the series of closed chambers. Means for filling and also emptying the chambers are provided in order to be able to increase the influence on the blood circulation. As a result thereof, the force exerted on the chest and/or the abdomen can be exactly chronologically limited to the systole and be quickly cancelled thereafter by means of emptying the chambers. Significant pressure is no longer exerted on the heart even though the lungs are then, for example, in a more or less filled condition because the thorax can again expand.

A possibility of further pressure increases inventively consist therein that the respirator is provided with a variable dead space or clearance volume. What is meant by a dead space is a quasi-buffer in the breathing gas line that stores a certain volume of $CO_2$ upon exhalation and resupplies it to the lungs during the following inhalation phase. In a simple case, this can be a matter of an elongation of the hose between the tracheal cannula and the respirator. Breathing gas can be supplied to the patient under higher pressures in a manner so that the emptying of the heart during the systole is further enhanced without the $CO_2$ content in the lungs sinking below a disturbing level.

BRIEF DESCRIPTION OF THE DRAWING

The FIGURE is a schematic illustration of a respirator in accordance with the present invention.

DESCRIPTION OF THE PREFERRED EMBODIMENT

The principles of the present invention are particularly useful in a respirator generally indicated at 1 in the FIGURE. The respirator 1 receives respiratory gas on a line 2, which is connected to an external gas source 40. Instead of the single gas line 2, a plurality of such lines for various components of the gas can be provided. The respiratory gas is supplied to the patient 6 through a valve arrangement 3 as well as a tracheal cannula 4 connected thereto and the tracheal cannula 4 terminates tightly in the trachea 5 of the patient 6. A cuff 7 can, for example, be provided for the termination of the trachea cannula 4 in the trachea 5. An eduction or ejection valve 8 is also connected to the tracheal cannula 4. The valve arrangement 3, which produces a metered feed of respiratory gas received in the line 2 from the pressurized source 40 can, for example, be of a known type such as disclosed in the International patent application No. PCT/SE82/00063. (W082/03014).

However, it is also possible to utilize an open cannula for spontaneous breathing. The open cannula has a thin additional cannula for the feed of the respiratory gas instead of a tracheal cannula terminating in the trachea and the eduction or ejection valve 8. The emptying of the lungs then occurs directly over the open cannula. Further, it is also possible to insert a thin cannula directly into the trachea in a surgical manner. The expiration then occurs over the natural breathing organs. In the two latter instances, a HFPPV respiration method (a high frequency positive pressure ventilation) is then advantageously employed.

The respirator 1 also includes a valve 9 which receives gas from an additional pressurized source 50 on a line 10. Compressed air is usually employed in the simplest case as the pressurized gas from the source 50. A line 11 leads from the valve 9 to a plurality of closed chambers 12 consisting of flexible material. The closed chambers 12 are disposed around the chest and/or partially around the abdomen of the patient 6. A hollow body 13 consisting of a rigid material which is matched to the shape of the thorax is situated around these chambers. A fluid can also be utilized for filling the chambers instead of pressurized gas. The eduction valve or ventilation valve 14 is again connected to the line 11 to enable exhaust or venting these chambers.

The ventilator or respirator 1 further contains an amplifier 15 to which the signals of a sensor are supplied. In the embodiment which is illustrated, two ECG electrodes 36 and 37 are applied to the patient's body and register the electrical heart signals and act as the sensor. These heart signals are processed by the amplifier and then applied to a detector 16 which detects the high electrical heart voltage during the systole and emit a pulse to an electronic circuit 17 or, respectively, a circuit 18. The circuits 17 and 18 each contain means for setting a selectable delay of the pulse coming from the detector 16. The valve arrangement 3 as well as the valves 8, 9 and 14 are driven by pulse-shaping circuits 19, 20 and 21, respectively. The pulse-shaping circuits 19–21 can, for example, by one-shot multivibrators with different pulse widths. In addition, the pulse-shaping circuits should contain means for setting the pulse width.

As illustrated, the output of the electronic circuit 17 goes to the pulse-shaper 20 whose output goes to both the pulse-shaper 21 and also to the valve 9. From the pulse-shaper 21, pulses go to the eduction valve 8 and also to the exhaust or eduction valve 14. In a similar manner, the signal from the detector 16 is applied to the electronic circuit 18, which has the time delay, and the output of the circuit 18 goes to the pulse-shaper 19, which applies a pulse to the valve arrangement 3.

The schematic illustration of the FIGURE also shows that the lungs 25 and 26 of the patient surround a large part of the heart of which the left ventricle 27 is shown. Pressure on the heart will occur due to the expansion of the lungs 25 and 26. Under normal conditions, however, this pressure increase is slight since the volume of the thorax easily enlarges particularly due to the outwardly directed movement of the thorax wall 28 and partially due to the downward directing movement of the diaphragm 29 into the abdomen cavity.

According to the invention, the thorax and the upper part of the abdomen are surrounded by a hollow body 13 which consists of a shapable envelope consisting of rigid material. This envelope is positioned around the body so that a certain expansion of the respiratory organs, i.e., the lungs and the chest and/or the abdomen, is possible without the envelope significantly impeding this expansion. When due to the application of the respiratory gas, this expansion has reached a certain amplitude, further expansion is prevented by the envelope as a result of which an increased pressure will occur inside the envelope and thus inside the thorax and around the heart.

The function of the respirator ventilator 1 and thus of the method utilizing the respirator is described in greater detail hereinbelow. The electrical activity of the heart at the beginning of the systole is registered by the electrodes 36 and 37 and initiates the feed of respiratory gas through the valve arrangement 3. The psychological delay between the electrical heart signal for the systole (the QRS complex) and the mechanical contraction of the heart is exploited in order to fill the lungs in one breath through the fast action of the valve arrangement 3. However, it is also possible to set a delay in the electrical circuits 17 and 18 so that the feed of the respiratory gas will occur during the systole that is related to the next following heartbeat.

At the same time as the feed of the respiratory gas or nearly simultaneously therewith, the elastic chamber 12 is filled with pressurized gas through the valve 9 and the line 11. The amount of gas supplied can also be regulated. An excess pressure will occur when the lungs expand because of the flow of the respiratory gas and this excess pressure is then amplified by the movement when the outwardly directed movement of the thorax wall 28 and/or downwardly directed movement of the diaphragm 29, respectively, is partially arrested by the hollow body 13 and by the filled chambers 12. This excess pressure is propagated through the cardiac wall so that the pressure on the blood enclosed in the heart will rise. By the correct setting of the electrical circuits such as 17, 18, 19, 20 and 21, the pressure increase on the heart will occur chronologically and synchronously with the pumping of the blood from the left ventricle into the large systemic aorta of the body. The blood in the systemic aorta 30 will then proceed to the important organs such as through additional artery 31 to the brain.

The various delay times and pulse durations are set according to the following principle. The amount of respiratory gas supplied to the patient at each respiration is defined by means of setting the valve arrangement 3 and/or the pressure in the line 2 so that the ventilation of the lungs suffices for a good gas exchange. The hollow body 13 is applied around the patient so that it adapts to the external contour of the body without exerting high pressure on the body at the beginning of each respiration cycle. The supply of air to the closed chambers 12 is likewise controlled so that the movement of the walls of the thorax and the diaphragm 29 during the feeding of the respiratory gas are restricted to such a degree that a suitable intensification of the pressure around the heart is generated during its pumping process.

The thorax itself is not compressed by the flexible chambers 12 to such a degree that the force thereby exerted produces an inwardly directed movement on the thorax wall 28. The flexible chambers 12 only fill out the cavity between the body surface and the hollow body 13. The flexible chambers 12 serve to limit the outwardly directed movement of the body surface in a definable and controllable manner. Moreover, they also serve to balance out certain inequities of the pressure on the body surface that could, for example, be produced by a rigid hollow body.

The pressure on the lungs 25 and 26 which occurs due to the supplying of the respiratory gas is composed of the pressure required for the expansion of the lungs and of the thorax walls and of the pressure arising in the thorax due to the hollow body 13 and the pressure chambers 12. The pressure gradient across the lung structure, however, does not exceed the gradient that occurs given a standard high-frequency ventilation in which experience has shown to be harmless. Any kind of deforming force that could damage the thorax wall is prevented by the pressure equalization of the air-filled, flexible chambers 12. An injurious effect on the blood circulation due to an impeded refilling of the heart ventricle is avoided in that every form of undesirable pressure on the thorax and in the thorax is prevented during the relaxation phase of the heart because the flexible chambers 12 are emptied through the exhaust valve 14 at the end of the systole. The lungs empty at the same time through the valve 8.

The electrical coupling according to the sample illustrated embodiment is as follows:

The output signal of the detector 16 proceeds over the two delay circuits 17 and 18, respectively, to the pulse-shaping circuits 19 and 20, respectively. The pulse-shaping circuit 19 determines the chronological duration during which the respiratory gas is supplied to the patient through the valve arrangement 3 and also determines the point in time to which this feed is to begin. Correspondingly, the circuit 20 determines when and how long the valve 9 should be opened. The point in time for opening the valves 14 and 8, respectively, is determined through a further circuit 21. At the same time it is presumed here that the valves 8 and 14, respectively, are closed when the arrangement 3 or, respectively, the valve 9 is opened.

The described sample embodiment is only of an explanatory nature. The support of the blood circulation strived for with the invention is also assured when the respirator is modified within the framework of the invention. For example, the sensors instead of being ECG electrodes could be connected to a heart pacemaker or a device which generates pulse to control the heart's activity. To provide a dead space or variable volume for receiving $CO_2$ exhaled from the lungs, the tube or cannula 4 may have an excess portion such as a loop 4a.

Although various minor modifications may be suggested by those versed in the art, it should be understood that we wish to embody within the scope of the patent granted hereon, all such modifications as reasonably and properly come within the scope of our contribution to the art.

We claim:

1. A respirator connectable to the lungs of a patient comprising:
   means for applying a respiratory gas to the lungs of said patient;
   means for restricting expansion of a substantial portion of the chest and abdomen of the patient by applying a continuous uniform non-deforming, volume limiting force to the chest and abdomen opposing expansion of the chest and abdomen; and
   control means for synchronizing the operation of said means for applying a respiratory gas and said means for restricting expansion so that the respiratory gas is applied at a point in the heart cycle of the patient such that the uniform force creates a pressure rise around the heart coinciding with the contraction phase of the heart.

2. A respirator as claimed in claim 1, wherein said means for applying a respiratory gas includes a valve arrangement operated by said control means.

3. A respirator according to claim 1, wherein said means for applying respiratory gas includes a tube extending into the lungs, said tube having a variable volume to enable retaining a portion of the exhaled gases for combination with respiratory gases during the next respiratory cycle.

4. A respirator as claimed in claim 1, wherein said control means includes at least one sensor means for obtaining at least one signal corresponding to a heart activity parameter.

5. A respirator according to claim 4, wherein the sensor means comprises ECG electrodes applied to the skin of the patient.

6. A respirator according to claim 4, further comprising means for generating electrical pulses for controlling the heart activity, and said sensor means being connected to the means for generating electrical pulses.

7. A respirator according to claim 4, wherein the sensor means is adapted for connection to an output of a heart pacemaker.

8. A respirator according to claim 1, wherein the means for restricting expansion includes a rigid hollow body surrounding at least a part of the chest and abdomen of the patient.

9. A respirator according to claim 8, wherein the hollow body contains a hardenable material that determines its shape.

10. A respirator according to claim 8, wherein the means for restricting expansion further includes a series of closed chambers consisting of flexible material disposed around the chest and abdomen of the patient inside the hollow body, said chambers being fillable with a gas or a fluid.

11. A respirator according to claim 10, wherein the means for restricting expansion further includes means for controlling the filling of the chambers during the applying of the respiratory gas to the patient and for emptying the chambers during an expiration phase of said patient.

12. A respirator according to claim 11, wherein the control means actuates the means for filling and for emptying the chambers.

13. A respirator according to claim 12, wherein the control means includes adjustable delay elements, said adjustable delay elements determining the point in time for applying respiratory gas, the duration of applying the respirator gas and the points in time for the filling and emptying of the chambers.

14. A respirator connectable to the lungs of a patient comprising:
a valve arrangement connected to a tube extending into the tracheae of said patient and connected to a source of respiratory gas, said tube permitting said respiratory gas to be supplied to the lungs of said patient;
means for restricting expansion of a substantial portion of the chest and abdomen of the patient by applying a continuous uniform non-deforming, volume limiting force to the chest and abdomen opposing expansion of the chest and abdomen;
sensor means for monitoring heart activity of said patient and for generating signals corresponding to said heart activity; and
control means connected to said valve arrangement, said means for restricting and said sensor means for synchronizing the operation of said valve arrangement and said means for restricting expansion in response to said signals from said sensor means such that the respiratory gas is supplied to said patient at a point in the heart cycle of the patient whereby the uniform force creates a pressure rise around the heart coinciding with the contraction phase of the heart.

* * * * *